United States Patent [19]

Camanzi et al.

[11] Patent Number: 5,185,130
[45] Date of Patent: Feb. 9, 1993

[54] SOLID-STATE SENSOR FOR DETERMINING HYDROGEN AND/OR $NO_x$ CONCENTRATION AND THE METHOD FOR ITS PREPARATION

[75] Inventors: Alberto Camanzi, Tor Lupara; Giorgio Sberveglieri, Cavriago, both of Italy

[73] Assignee: Eniricerche S.p.A., Milan, Italy

[21] Appl. No.: 447,855

[22] Filed: Dec. 8, 1989

[30] Foreign Application Priority Data

Dec. 23, 1988 [IT] Italy ............................ 23090 A/88

[51] Int. Cl.⁵ .................... B05D 3/02; G01N 27/12
[52] U.S. Cl. ................................... 422/90; 422/95; 422/98; 427/124; 427/250; 427/255; 427/376.7
[58] Field of Search ........................ 422/90, 95, 98; 427/374.6, 376.2, 124, 250, 255, 376.7

[56] References Cited

U.S. PATENT DOCUMENTS

| | | |
|---|---|---|
| 3,901,067 | 8/1975 | Boardman, Jr. et al. |
| 4,030,340 | 6/1977 | Chang |
| 4,169,369 | 10/1979 | Chang et al. |
| 4,387,165 | 6/1983 | Youngblood ..................... 422/98 |
| 4,579,751 | 4/1986 | Forster |

FOREIGN PATENT DOCUMENTS 0115953  8/1984  European Pat. Off.
2177215  1/1987  United Kingdom.

OTHER PUBLICATIONS

Madou, et al., *Chemical Sensing with Solid State Devices*, Academic Press, pp. 5-7.

Sberveglieri, et al., "Bismuth-doped tin oxide thin-film gas sensors," *Sensors and Actuators B*, 3 (1991) pp. 183-189.

Sberveglieri, et al., Journal of Materials Science Letters, 10 (1991) pp. 602-604.

*Primary Examiner*—Jill A. Johnston
*Attorney, Agent, or Firm*—Oblon, Spivak, McClelland, Maier & Neustadt

[57] ABSTRACT

A solid-state sensor is described for determining hydrogen and/or $NO_x$ concentration and the method for its preparation, it comprising a support on which a thin film of thickness between 80 and 200 nm is deposited consisting of tin (Sn) and bismuth (Bi) oxides, the quantity of bismuth in the thin film being between 5 and 7% in terms of atomic weight.

4 Claims, 8 Drawing Sheets

SOLID-STATE SENSOR FOR DETERMINING HYDROGEN AND/OR $NO_x$ CONCENTRATION AND THE METHOD FOR ITS PREPARATION

This invention relates to a solid-state sensor comprising a thin film of $SnO_2$ doped with bismuth for determining hydrogen and/or $NO_x$, and the method for its preparation.

The construction of easy-to-read portable instruments able to measure hydrogen even under critical environmental conditions relies on the development of low-cost sensors of high reliability. There are many situations in which fast and frequent measurement of hydrogen, including at low concentration, is necessary. For example, instruments able to measure hydrogen at the walls of reactors in which chemical processes are taking place, or at the walls of pipes in which $H_2S$-releasing processes are occurring appear to be of great industrial interest. Again, environmental safeguard and protection could be improved by using fast, robust and reliable methods for detecting gas evolvement. Finally, instruments which monitor hydrogen production in certain reactions would enable industrial processes to be optimized in numerous cases.

As stated, instruments of this type are based on gas detectors such as sensors and in particular solid-state sensors.

Recent published works show that research and technological development on solid-state hydrogen sensors have been directed towards production of the following types of sensor:
protonic (galvanic)
oxide semiconductor
field effect (MISFET) semiconductor In spite of the apparent ability of these systems to satisfy various requirements, commercially available hydrogen-sensitive sensors which respond selectively to hydrogen without interference by other gases, without requiring a constant oxygen flow, without the need for appropriate operating temperatures or a relative humidity which is not too high, etc., are still not completely satisfactory.

In particular, in the case of surface-layer sensors based on transistors such as FETs (see for example Solid State Chemical Sensors—Ed. J. Janatan and R. Muber—1985; Journal of Molecular Electronics—Vol. 2, 1986, 51—A. Sibbald), commercial devices in the true sense of the term are still not available (Solid State Gas Sensors, Ed. P. Mosley and B. C. Tofield, 1987—The Adam Hilger—Bristol).

The only types of commercially available semiconductor sensor are those of the Taguchi series, also produced by Figaro. However they still do not seem to give properly reproducible results in terms of response by an individual sensor or in terms of comparison between sensors having the same characteristics. Their production technology is not yet considered sufficiently reliable. In other words, oxide semiconductor sensors do not appear suitable for most industrial applications, in particular for monitoring explosive or flammable gases, or generally in the control of processes in which $H_2$, $O_2$ and CO are involved.

The main problems of solid-state sensors, whether these are based on FETs or on oxide semiconductors, can be summarised as follows:
response saturation at concentrations of around 1% of hydrogen in air or in nitrogen;
instability of the device with time (drift);
high recovery times;
poor response reproducibility;
protective encapsulation against contaminants but sufficient permeability towards the gases to be measured.

The progress made in constructing galvanic or semiconductor (FET or oxide) sensors has been considerable in the last ten years. These types of sensor are currently the only ones susceptible to commercial development, because of their cost and robustness.

It can be concluded that:
current devices and already tested prototypes require further research for understanding their operation, and considerable investment for their marketing [V. Lantto, P. Romppainen, S. Leppavuori, Sensors and Actuators, 15 (1988) p. 347];
microfabrication technology appears to be the compulsory choice in the production of widely marketed, low-cost sensors; it would allow greater progress in structural design and geometrical configuration, and in performance.

A patent application has recently been published (GB 2177215) claiming a solid-state sensor specific for CO determination and having as its sensing element tin oxide to which bismuth oxide has been added to the extent of about 15% by weight (corresponding to 13.8% of Bi).

We have now discovered a solid-state sensor for determining hydrogen concentration which obviates most of the drawbacks of preceding sensors.

Our sensor, which also uses tin oxide and bismuth oxide as sensing elements but in different concentrations from those of GB 2177215, enables hydrogen and/or $NO_x$ to be determined even if CO and/or $CH_4$ are present; i.e. we have found that by using lesser percentages of $Bi_2O_3$, not only does the sensor have high sensitivity towards $H_2$ but also has high selectivity in sensing $H_2$ in the presence of $CH_4$ and in particular in the presence of CO.

The sensor which we claim is:
robust
miniaturizable
of low cost
selective towards $H_2$ and/or $NO_x$ in the presence of CO and/or $CH_4$
sensitive to low hydrogen concentrations
of low intrinsic power consumption.

The solid-state sensor for determining hydrogen and/or $NO_x$ concentration according to the present invention is characterised by comprising a support on which a thin film of thickness between 80 and 200 nm is deposited consisting of tin and bismuth oxides, the quantity of bismuth in the thin film being between 5 and 7% in terms of atomic weight (corresponding to 8.3–11.7% by weight).

The types of support (or substrate) on which the films are deposited do not influence the response of the device provided their surface roughness is less than $5\mu$. The supports which can be used include for example glass, alumina and other ceramics. The aforesaid solid-state sensor can be prepared by the following procedure, which constitutes a further subject matter of the present invention.

This procedure essentially comprises depositing a thin film of Sn and Bi with a Bi content of 5–7% by atomic weight on a ceramic vitreous support by vacuum evaporation followed by thermally treating the film deposited on the support, the thermal treatment being effected in accordance with the following cycle:

increasing the temperature from ambient to between 300° and 350° C. over a time of between 5 and 35 minutes ($t_1$);

maintianing the temperature of between 300° and 350° C. for a time of between 1 and 3 hours ($t_2$);

increasing the temperature to between 400° and 450° C. over a time of between 2.5 and 3.5 hours ($t_3$);

maintaining the temperature of between 400° and 450° C. for a time of between 2.5 and 3.5 hours ($t_4$);

increasing the temperature to between 470° and 500° C. over a time of between 4 and 6 hours ($t_5$);

maintaining the temperature of between 470° and 500° C. for a time of between 3 and 4 hours ($t_6$);

cooling to ambient temperature over a time of between 1.5 and 2.5 hours ($t_7$).

The film can be deposited on the substrate by vacuum evaporation using for example one of the following methods:

a) rapid evaporation of premolten Sn-Bi alloy;
b) multilayer sequential evaporation of the two metals Sn and Bi.

a) Rapid Evaporation of Premolten Sn-Bi Metal Alloy

This method consists of premelting an Sn-Bi metal alloy in an environment at a pressure of $10^{-6}$–$10^{-7}$ mbar and then evaporating said alloy onto a substrate of the aforesaid type maintained at a temperature of between 90° and 110° C.

The performance of the device in terms of hydrogen response sensitivity is determined by the speed of film deposition, which must be equal to or greater than 50 nm/sec.

b) Multilayer Sequential Evaporation of the Two Metals Sn and Bi

This method consists of thermally evaporating the two metals Sn and Bi sequentially in an environment at a pressure of $10^{-6}$–$10^{-7}$ mbar to form sandwich structures, with the Bi thickness less by preferably about one order of magnitude than the thickness of the Sn which encloses it. The metals are evaporated from separate crucibles.

Some examples are given hereinafter to better illustrate the invention but are not to be taken as limitative thereof. In the following examples the sensitivity is defined as:

(electric current in hydrogen-electric current in air)
───────────────────────────────────────────
electric current in air
expressed as a percentage, i.e.:
$\Delta I / I$ (air) × 100%

The sensitivity is determined by measuring the current passing through the sample to which a potential difference is applied. The sensor is placed on a heating device inside a chamber through which the gas flows.

The required gas concentration is obtained by regulating the flows from cylinders containing predetermined concentrations of the gases.

The relative humidity in the measuring chamber is obtained by passing a controlled flow of synthetic air through a porous baffle placed in bidistilled water and measuring the R.H. by a capacitive probe located in the chamber.

EXAMPLE 1

Sensors were produced with films obtained on an $Al_2O_3$ substrate by method a) (rapid evaporation of premolten Sn-Bi metal alloy) with 7 atomic wt % of Bi using the following thermal treatment:

($t_1$) increasing temperature from ambient to 350° C. over 6 minutes;
($t_2$) maintaining 350° C. for 2 hours;
($t_3$) increasing temperature to 450° C. over 3 hours;
($t_4$) maintaining 450° C. for 3 hours;
($t_5$) increasing temperature to 500° C. over 5 hours;
($t_6$) maintaining 500° C. for 3.5 hours;
($t_7$) cooling the sensor to ambient temperature over 2 hours.

The final film structure has a morphology in the form of agglomerates of 1–10$\mu$ in size uniformly distributed over a surface of the same composition, with a covering factor (defined as the area of agglomerates per unit surface area) of 0.6–0.8. In this manner the true "active" absorption area is much greater than a flat film.

The crystallographic structure is that of a polycrystalline two-phase compound of $SnO_2$ and $BiO_3$, with preferential $SnO_2$ orientation in the 101 direction (textured polycrystal).

Figure 1:
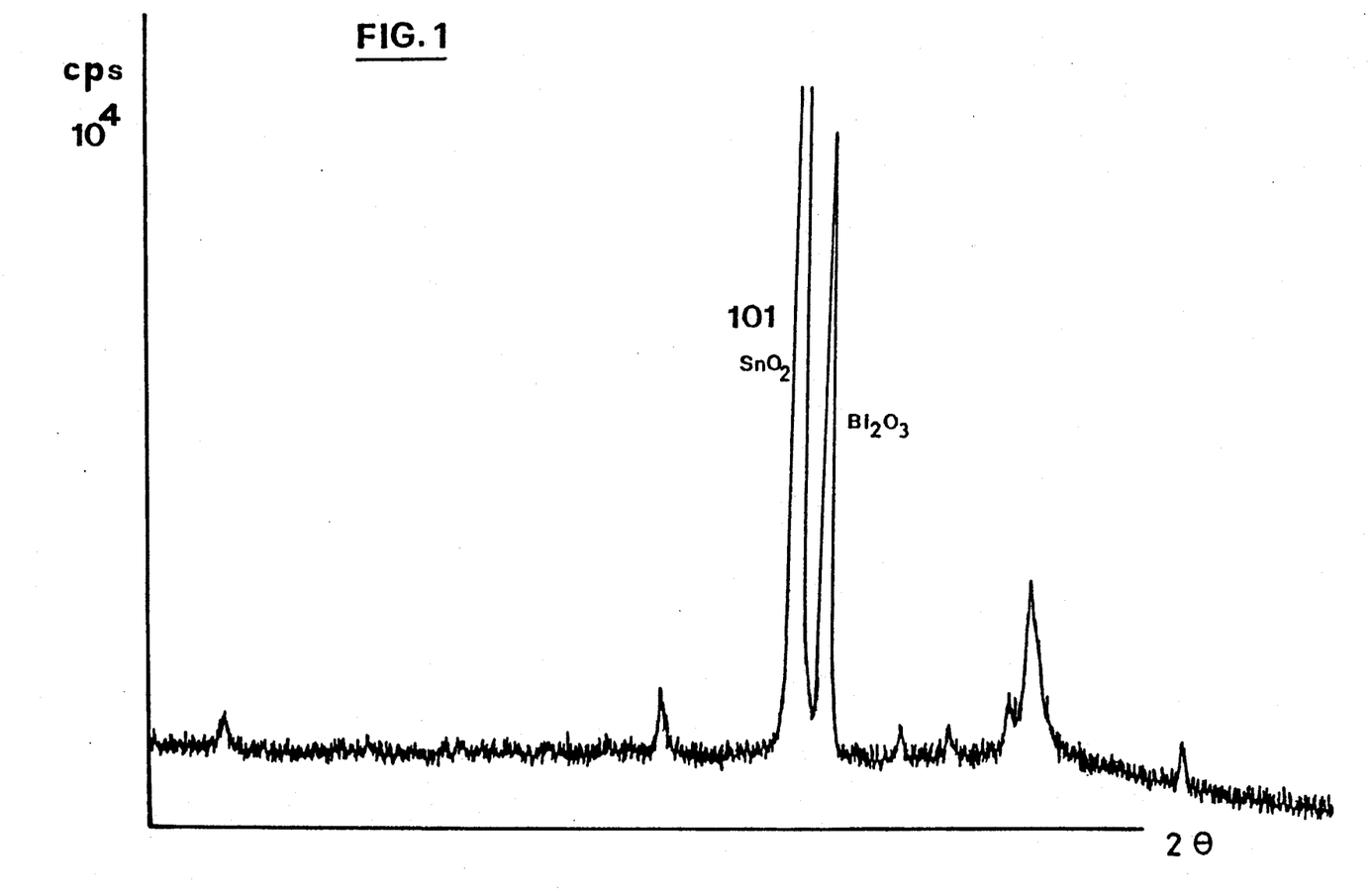
Figure 2:
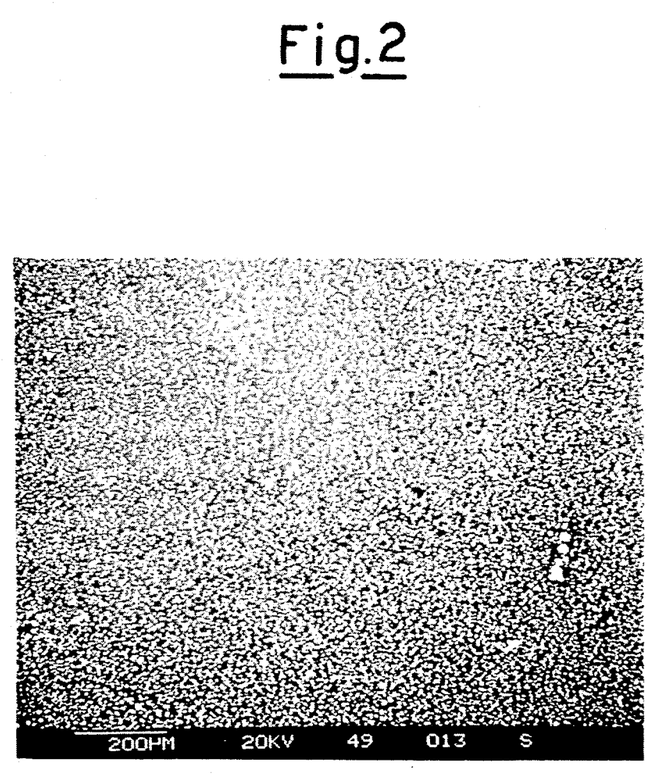

The deposition rate (nm/sec) is 55.
The results obtained are as follows:
Film thickness: 200 nm
Sensitivity (at 1000 ppm $H_2$ in air): 15000%
FIG. 1 shows the corresponding X-ray diffraction spectrum, while FIG. 2 shows the film morphology and the volumetric distribution of the bismuth oxide.

EXAMPLE 2 (COMPARATIVE)

Example 1 was followed but with a different deposition rate, to give the following results:
Deposition rate (nm/sec): 30
Sensitivity (at 1000 ppm $H_2$ in air): 400%
It can be seen that with a deposition rate of less than 50 nm/sec the sensitivity decreases considerably.

EXAMPLE 3 (COMPARATIVE)

Figure 3:
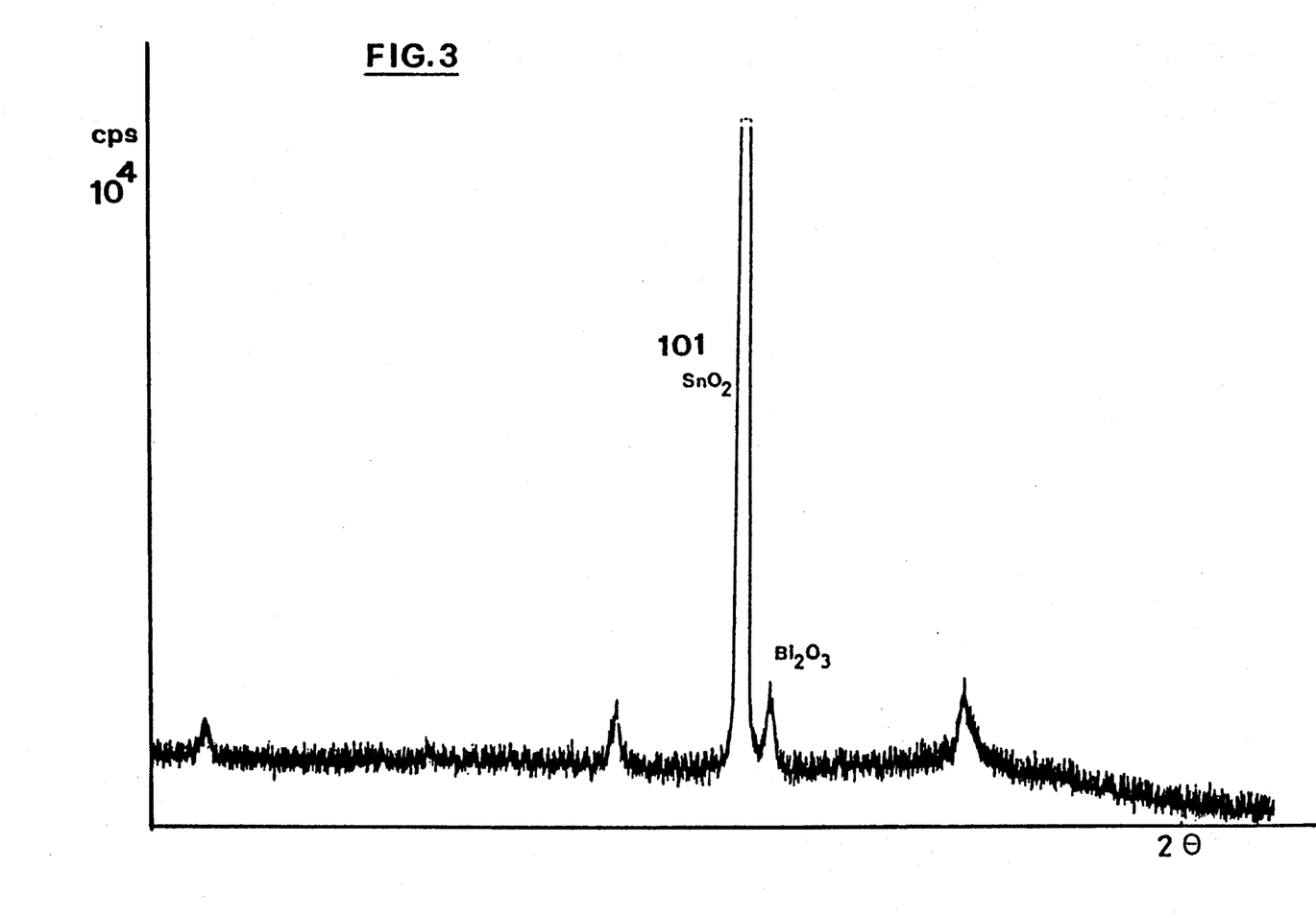
Figure 4:
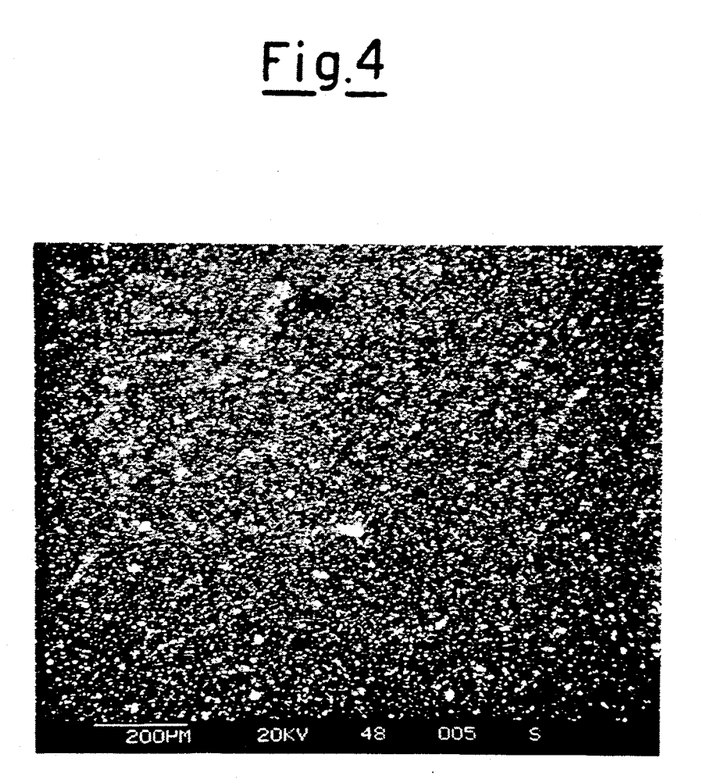

Example 1 was followed but with a different thermal cycle. The thermal cycle, which was uncontrolled, was effected with a $t_1$ of 80 minutes.
The deposition rate (nm/sec) was 55.
The results obtained were:
Film thickness: 200 nm
Sensitivity (at 1000 ppm $H_2$ in air): 550%
FIG. 3 shows the corresponding X-ray diffraction spectrum, while FIG. 4 shows the film morphology and the volumetric distribution of the bismuth oxide.

It can be seen that the volumetric distribution of the bismuth oxide is both less than and less uniform than that of Example 1, FIG. 2.

EXAMPLE 4

Figure 5:
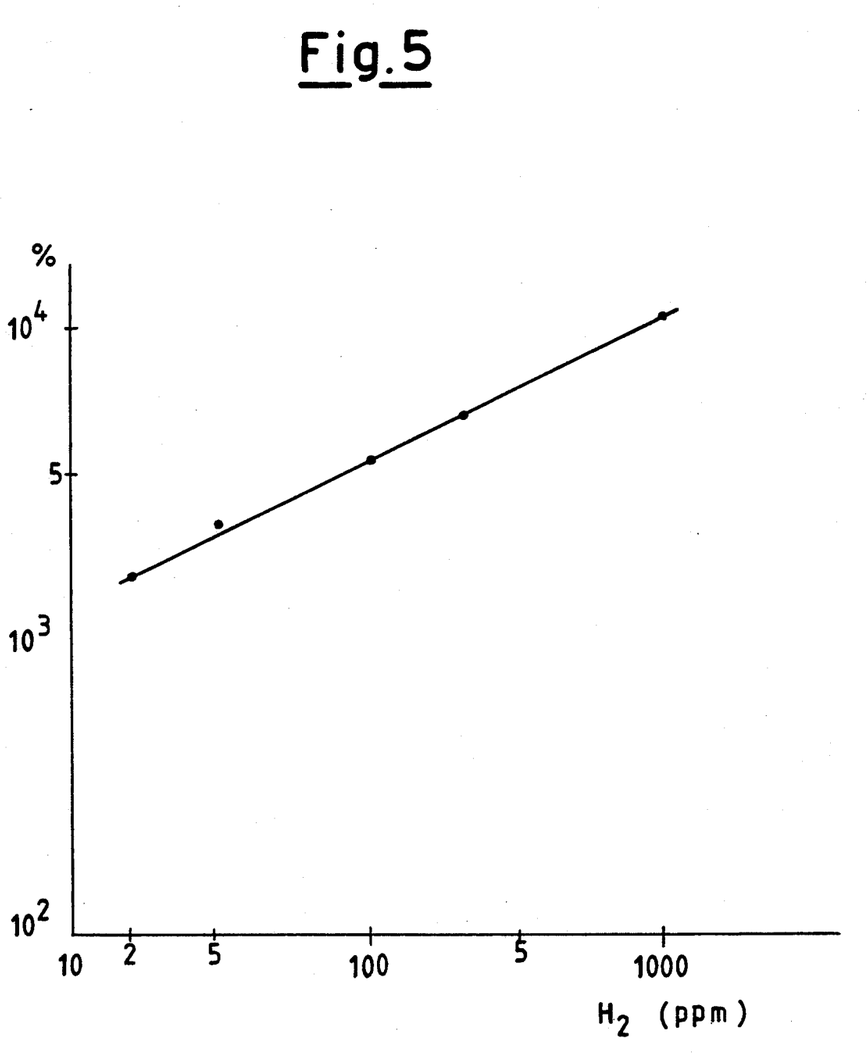

A sensor was produced with its film obtained on an $Al_2O_3$ substrate by method a) (rapid evaporation of premolten Sn-Bi metal alloy), using the thermal treatment of Example 1.
% bismuth in film: 5%
Deposition rate: about 80 nm/sec.
Film thickness: 200 nm
FIG. 5 shows a typical curve of sensitivity against hydrogen concentration in air, ranging from 20 ppm to 1000 ppm.

EXAMPLE 5

A sensor was produced with its film obtained on an $Al_2O_3$ substrate by method b) (multilayer sequential evaporation of the two metals Sn and Bi) (first layer Sn of 90 nm thickness, second layer Bi of 9.5 nm thickness), using the thermal treatment of Example 1.

% bismuth in film: 7%
Film thickness: 100 nm

Figure 6:
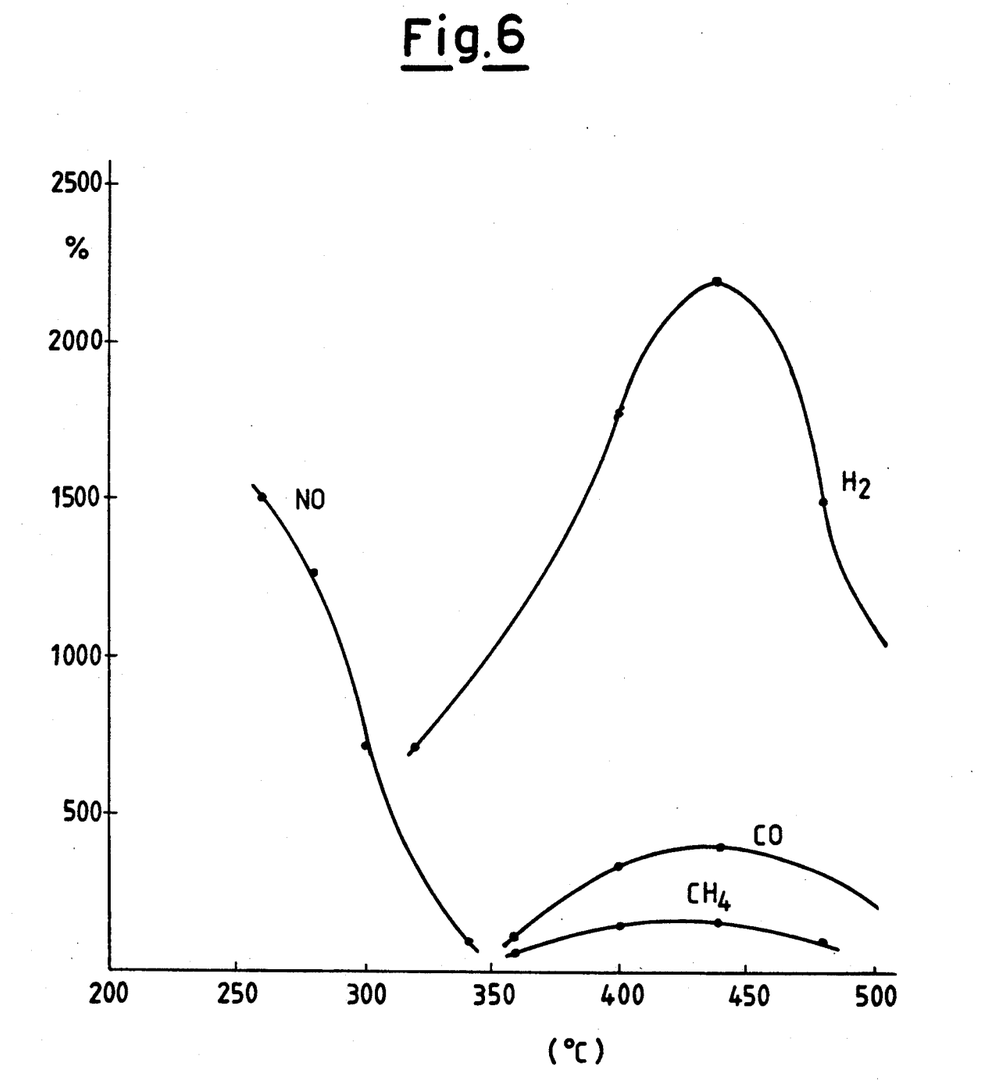

FIG. 6 shows sensitivity curves for 1000 ppm of $H_2$, NO, CO and $CH_4$ in air against operating temperature within the range of 200°–500° C.

The following conclusions can be drawn:

a) sensitivity towards hydrogen is at least one order of magnitude greater than that for the other gases at the same operating temperature;

b) the operating temperature at which maximum sensitivity and selectivity for hydrogen is obtained is about 450° C.;

c) sensitivity towards NO and $NO_2$ is very high, but only if the operating temperature is between 200° and 250° C., rather than at 450° C.

The same measurements effected not in dry air but in moist air with a relative humidity of 30% show a general reduction in sensitivity towards the reducing gases of about 10%, but a slight increase for the nitrogen oxides.

Thus the choice can be made between nitrogen oxides and hydrogen on the basis of the operating temperature, and the choice can be made between CO, $CH_4$ and hydrogen on the basis of the sharp differences in response.

EXAMPLE 6

Sensor selectivity was measured by subjecting the sensor of Example 5 to the following gas exposure sequence:

immersion in air;
immersion in $H_2$ and air;
immersion in $H_2$, CO and air;
immersion in $H_2$ and air;
immersion in $H_2$, $CH_4$ and air;
immersion in $H_2$ and air;
immersion in air.

The following table shows the results obtained:

| Voltage (volts) | Current (μA) | Gas (ppm) | G ($\mu$ ohm$^{-1}$) |
|---|---|---|---|
| 15 | 2 | air | 0.13 |
| 15 | 32.9 | 100 $H_2$ | 2.19 |
| 15 | 33.4 | 100 $H_2$ + 400 CO | 2.22 |
| 15 | 32.9 | 100 $H_2$ | 2.19 |
| 15 | 34 | 100 $H_2$ + 200 $CH_4$ | 2.26 |
| 15 | 31.8 | 100 $H_2$ | 2.12 |
| 15 | 4.8 (after 1) | air | 0.32 |

Good response reversibility can be noted as can the limited effect due to 200 ppm of $CH_4$ and 400 ppm of CO in 100 ppm of $H_2$.

EXAMPLE 7

A sensor was produced with its film obtained on an $Al_2O_3$ substrate by method b) (multilayer sequential evaporation of the two metals Sn and Bi) (first layer Sn of 43 nm thickness, second layer Bi of 7 nm thickness, third layer Sn of 50 nm thickness).

% bismuth in film: 5%
Film thickness: 100 nm

Figure 7:
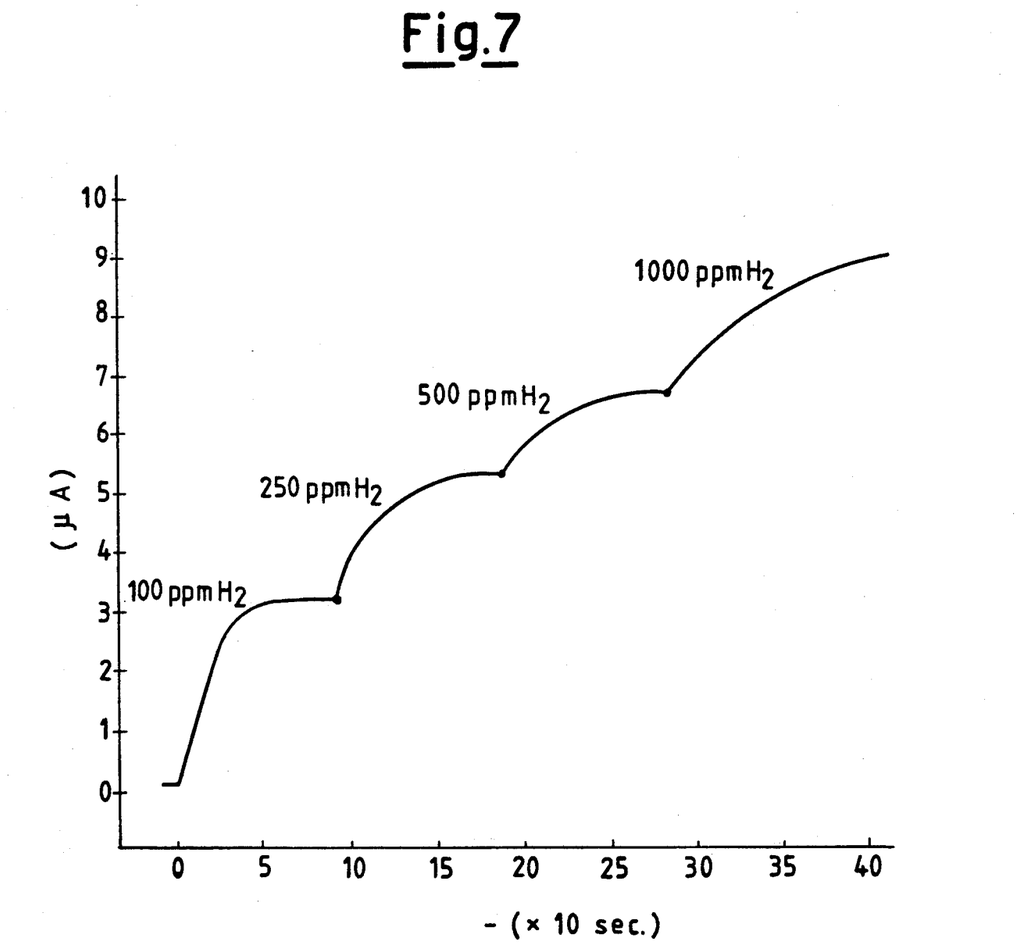

FIG. 7 shows the isothermal adsorption curve (t=400° C.) for hydrogen at increasing concentrations of hydrogen in air, i.e. the curve of sensor response for varying hydrogen parital pressure.

EXAMPLE 8

Figure 8:
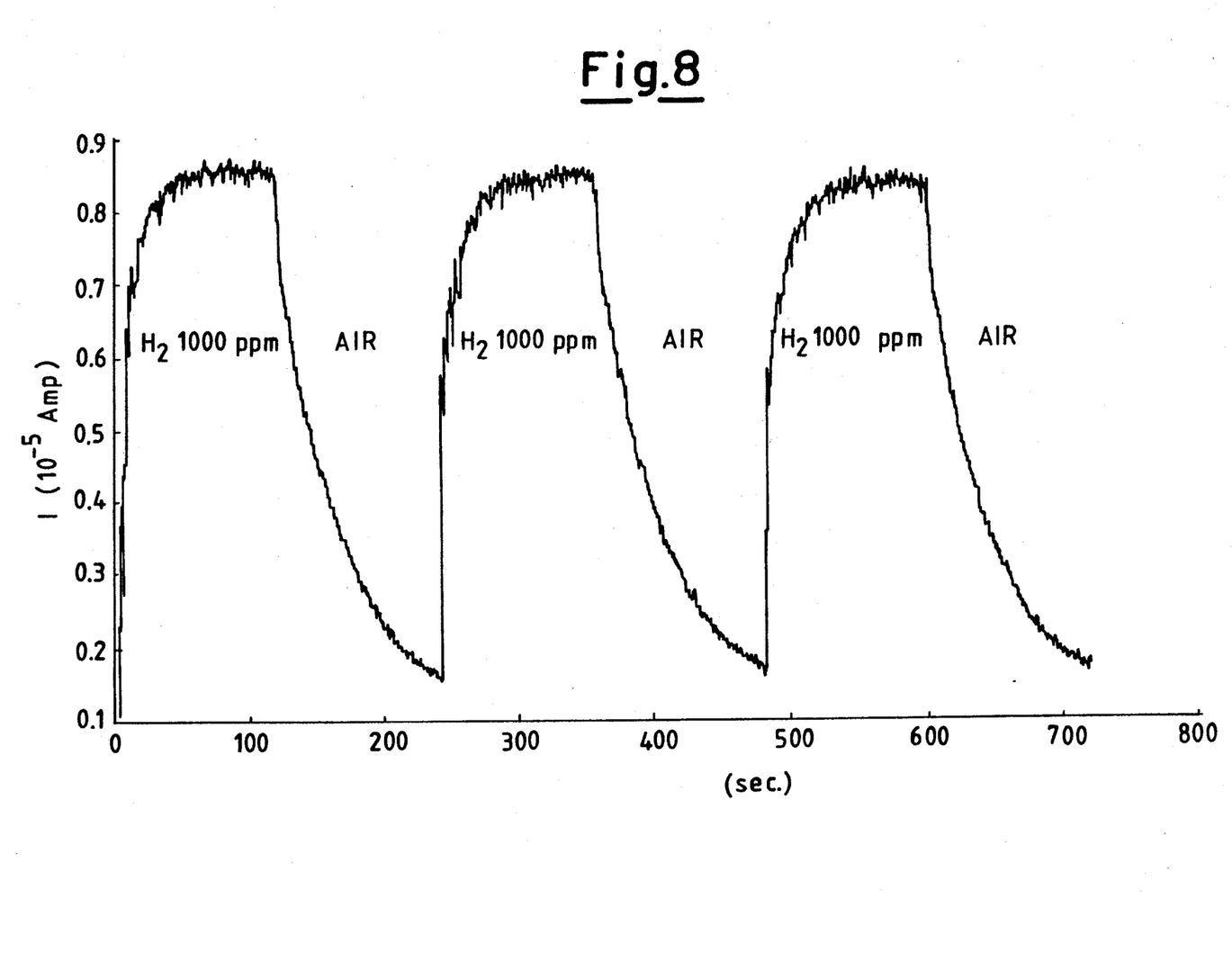

FIG. 8 shows the curve of electric current against time for a succession of 1000 ppm hydrogen-in-air cycles of constant duration effected with a sensor of the type used in Example 7. The curve shows the reproducibility of the response throughout several hydrogen-air cycles, and of the response and recovery times for a hydrogen concentration of 1000 ppm in air.

In gas measurement the response time is generally defined as the time required to attain 90% of the final value, i.e. of the relative current variation which follows a determined variation in the gas concentration at the sensor.

As the example shows, only a few seconds are required to obtain a response variation of 90% of the final value for a hydrogen concentration of 1000 ppm in dry air.

The time for recovery to the initial value in an air stream is about 2–3 minutes and can be further reduced if the sensor is heated to above its operating temperature (but not beyond 550° C.).

We claim:

1. A solid-state sensor for determining the concentration of a gas selected from the group consisting of hydrogen and $NO_x$, comprising a support on which a thin film, of thickness between 80 and 200 nm, is deposited, said thin film consisting of tin oxide and bismuth oxide, wherein the molar ratio of bismuth to tin is from 5:95 to 7:93.

2. A method for preparing the solid-state sensor of claim 1 comprising, depositing a thin film of Sn and Bi on a ceramic vitreous support by vacuum evaporation, said thin film having a molar ratio of Bi to Sn of from 5:95 to 7:93, and, in an oxygenated environment, thermally treating the film deposited on the support, the thermal treatment being effected in accordance with the following cycle:

increasing the temperature from ambient to between 300° and 350° C. over a time of between 5 and 35 minutes;

maintaining the temperature of between 300° and 350° C. for a time of between 1 and 3 hours;

increasing the temperature to between 400° and 450° C. over a time of between 2.5 and 3.5 hours;

maintaining the temperature of between 400° and 450° C. for a time of between 2.5 and 3.5 hours;

increasing the temperature to between 470° and 500° C. for a time of between 4 and 6 hours;

maintaining the temperature of between 470° and 500° C. for a time of between 3 and 4 hours;

cooling to ambient temperature over a time of between 1.5 and 2.5 hours.

3. A method as claimed in claim 2, wherein the vacuum evaporation is effected at a deposition rate of at least 50 nm/sec by evaporating an Sn and Bi alloy, previously melted at a pressure of between $10^{-6}$ and $10^{-7}$ mbar, onto a substrate maintained at a temperature of between 90° and 110° C.

4. A method as claimed in claim 2, wherein the vacuum evaporation is effected by multilayer sequential evaporation of the two metals Sn and Bi at a pressure of between $10^{-6}$ and $10^{-7}$ mbar in such a manner as to form a sandwich structure with a Bi:Sn thickness ratio of from 1:1 to 1:10.

* * * * *